(12) United States Patent
Lazo et al.

(10) Patent No.: US 6,642,033 B1
(45) Date of Patent: Nov. 4, 2003

(54) NUCLEIC ACIDS FOR DETECTING PARVOVIRUS AND METHODS OF USING SAME

(75) Inventors: Aristides Lazo, West Newton, MA (US); Xiaojuan Zhao, Queens, NY (US); Jodie Ann Tassello, Boston, MA (US); Veronica Gibaja, Dorchester, MA (US)

(73) Assignee: V.I. Technologies, Inc., Watertown, MA (US)

( * ) Notice: Subject to any disclaimer, the term of this patent is extended or adjusted under 35 U.S.C. 154(b) by 0 days.

(21) Appl. No.: 09/619,420

(22) Filed: Jul. 19, 2000

Related U.S. Application Data
(60) Provisional application No. 60/144,721, filed on Jul. 20, 1999.

(51) Int. Cl.$^7$ .................. C12P 19/34; C12Q 1/68; C07H 21/04
(52) U.S. Cl. .................. 435/91.1; 435/91.2; 435/6; 536/23.1; 536/24.33
(58) Field of Search .................. 435/6, 91.1, 91.2; 536/24.33, 23.1

(56) References Cited

FOREIGN PATENT DOCUMENTS

| WO | 84/02847 | * | 8/1984 |
| WO | 96/09391 | * | 3/1996 |
| WO | WO 98/05769 | | 2/1998 |
| WO | WO 98/24913 | | 6/1998 |

OTHER PUBLICATIONS

Edison et al., "Multiple primer pairs for polymerase chain reaction (PCR) amplification of human parvovirus B19 DNA", Journal of Virological Methods, vol. 44, pp. 155–165 (1993).*

McOmish et al., "Detection of Parvovirus B19 in Donated Blood: a Model System for Screening by Polymerase Chain Reaction", Journal of Clinical Microbiology, pp. 323–328 (1993).*
Summers, et al., J. gen. Virol., 64: 2527–2532 (1983).
Cotmore and Tattersall., Science, 226:1161–1165 (1984).
Deiss, et al., Virol., 175:247–254 (1990).
Morinet, et al., Archives of Virol., 90:165–172 (1986).
Gallinella, et al., J. Virol. Methods, 41:203–211 (1993).
Saldanha and Minor, British Journal of Haematology, 93:714–719 (1996).
Tyagi and Kramer, Nature Biotechnology, 14:303–308 (1996).
Yamakawa, et al., Obstetrics & Gynecology, 86:126–129 (1995).
Brown, et al., Crit. Rev. Oncol. Hematol. 16:1–31 (1994).
McOmish, et al., J. Clin. Microbiol., 31:323–328 (1993).
Kerr, et al., J. Virol. Methods, 53:213–222 (1995).
Bergeron, et al., Virology, 197:86–98 (1993).
Carriere, et al., J. Virological Methods, 44:221–234 (1993).
Durigon, et al., J. Virological Methods, 44:155–165 (1993).
Hemauer, et al., J. General Virology, 77:1781–1785 (1996).
Nikkari and Ekblad, Am. J. Perinatology, 12:447–449 (1995).
Nguyen, et al., The Lancet, 352:1524 (1998).
Shade, et al., J. Virology, 58:921–936 (1986).

* cited by examiner

*Primary Examiner*—Kenneth R. Horlick
*Assistant Examiner*—Cynthia Wilder
(74) *Attorney, Agent, or Firm*—Mintz, Levin, Cohn, Ferris, Glovsky and Popeo; Ivor R. Kirifi; David E. Johnson (57) ABSTRACT

Disclosed are nucleic acids that can be used as probes for detecting parvovirus in a sample of nucleic acid molecules. The nucleic acids hybridize to regions encoding a non-structural protein or structural proteins of human parvovirus strain 19 or porcine parvovirus. Also disclosed are methods for detecting and amplifying parvovirus in a sample using the nucleic acids of the invention.

24 Claims, 1 Drawing Sheet

Fig. 1

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: VINS-3F
      OLIGO

<400> SEQUENCE: 1
atggagctat ttagaggggt                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: VINS-3R
      PRIMER

<400> SEQUENCE: 2
gttcccagtc agaagtgtct                                              20

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: PRV3

<400> SEQUENCE: 3
taatgttctg gactgtgcta acgat                                        25

<210> SEQ ID NO 4
```

```
<211> LENGTH: 24
<212> TYPE: DNA
<213> ORGANISM: Artificial Sequence
<220> FEATURE:
<223> OTHER INFORMATION: Description of Artificial Sequence: VIVP-1F

<400> SEQUENCE: 4
cccagagcac cattataagg tgtt                                          24

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: VIVP- 1R

<400> SEQUENCE: 5
ttatgggact aatggtgcaa acc                                           23

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: VIVP-1P
      PROBE

<400> SEQUENCE: 6
cacaatgcca gtggaaagga ggcaa                                         25

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: VIPPVP-1F
      PRIMER

<400> SEQUENCE: 7
gaccaaggag aaccaactaa                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: VIPPVP-1R
      PRIMER

<400> SEQUENCE: 8
ttcatcagct gctgagaagt                                               20

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: VIPPVP-1P

<400> SEQUENCE: 9
aaaagaacac gacgaagcct acgacaaata                                    30

<210> SEQ ID NO 10
<211> LENGTH: 20
<212> TYPE: DNA
<213> ORGANISM: Artificial Sequence
<220> FEATURE:
```

-continued

```
<223> OTHER INFORMATION: Description of Artificial Sequence: VIPPVP
      F(Alt) PRIMER

<400> SEQUENCE: 10
acaggactaa ctctaccagg                                              20
```

US 6,642,033 B1

NUCLEIC ACIDS FOR DETECTING PARVOVIRUS AND METHODS OF USING SAME

RELATED APPLICATIONS

This application claims priority to U.S. application Ser. No. 60/144,721, filed Jul. 20, 1999. The contents of this application are incorporated by reference in their entirety.

FIELD OF THE INVENTION

The present invention relates generally to nucleic acids and more specifically to nucleic acid molecules that can be used as probes for detecting and amplifying parvovirus.

BACKGROUND OF THE INVENTION

The parvoviruses constitute a family of viruses that have been associated with diseases or conditions in multiple mammals, including dogs and humans. Parvovirus strain B19 is associated with diseases and syndromes in humans. Parvovirus strain B19 is an iscoahedral, non-enveloped DNA virus whose genome includes a single-stranded 5.6 kb DNA molecule that encodes two structural proteins, which are designated VP1 and VP2. Also encoded in the parvoviral genome is a non-structural protein, designated NS-1, which is considered important for viral DNA replication.

Several diseases and syndromes associated with parvovirus strain B19, have been described. One disease includes ertyhema infectiosum (EI), which is a common in children and is characterized by fever, headache, nausea, and diarrhea. While these symptoms are typically mild, the consequences of parvovirus infection in some individuals, such as pregnant women, can be more severe. For example, parvovirus B19 infection during pregnancy can have significant and potentially fatal effects on the fetus.

SUMMARY OF THE INVENTION

The invention is based in part on the discovery of oligonucleotides that can be used to detect and amplify human parvovirus B19 in a biological sample. The nucleic acids of the invention are referred to herein as PRVX nucleic acids. PRVX nucleic acids of the invention can be used to detect parvovirus in biological samples, such as those containing blood and blood-derived products.

Accordingly, in one aspect the invention features nucleic acids that specifically hybridize to regions of human B19 parvovirus encoding NS and VP. Nucleic acids of the invention include PRV1, PRV2, and PRV3 nucleic acids. Examples of PRV1 and PRV2 nucleic acids of the invention include the primers VINS-3F and VINS-3R, respectively. These primers can be used to amplify a 106 nucleotide sequence from a region encoding a non structural ("NS") protein of a human B19 parvovirus. In some embodiments, amplification occurs in a polymerase chain reaction ("PCR"). The VINS-3F oligonucleotide includes the nucleotide sequence 5'-ATGGAGCTATTTAGAGGGGT-3' (SEQ ID NO:1). The VINS-3R oligonucleotide primer includes the sequence 5'-GTTCCCAGTCAGAAGTGTCT-3'(SEQ ID NO:2). These sequences are highly conserved among human parvovirus strain B19 isolates.

The PCR product generated using VINS-3F and VINS-3 can be detected using a PRV3 nucleic acid of the invention. The PRV3 nucleic acid is based on the nucleotide sequence 5'-TAATGTTCTGGACTGTGCTAACGAT-3' (SEQ ID NO:3), which recognizes a nucleotide sequence in the region amplified by the VINS-3F and VINS-3R primers.

Figure 1:
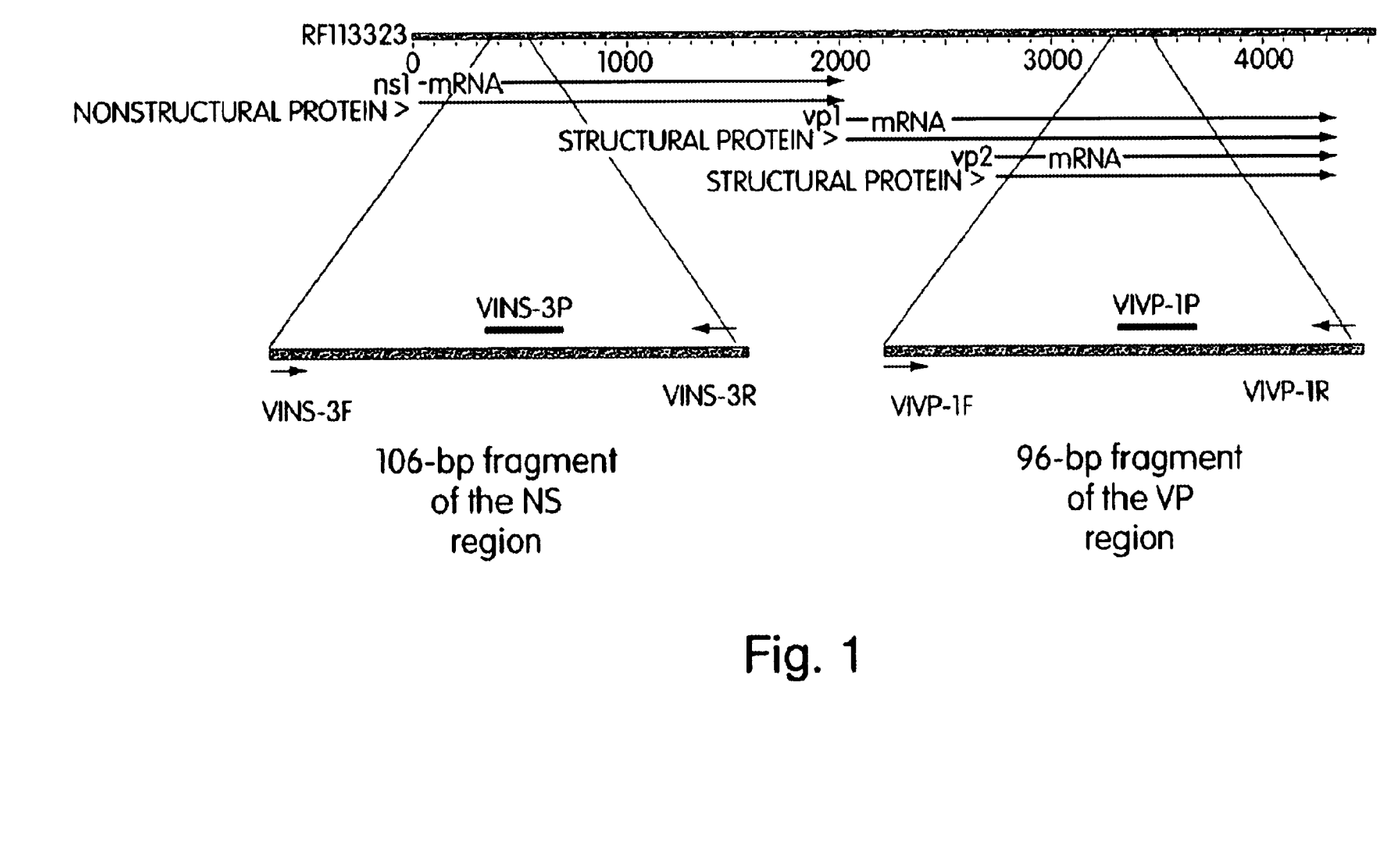

Also within the invention are PRV4, PRV5, and PRV6 nucleic acids. These nucleic acids are based on oligonucleotides derived from a region of the human B19 parvovirus encoding the viral protein (VP). PRV4 and PRV5 nucleic acids include VIVP-1F and VIVP-1R, respectively. A VIVP-IF nucleic acid includes the sequence 5'-CCCAGAGCACCATTATAAGGTGTT-3'(SEQ ID NO:4), which is highly conserved among parvovirus B19 isolates. A VIVP-IR nucleic acid includes the sequence 5'-TTATGGGACTAATGGTGCAAACC-3' (SEQ ID NO:5), which is also highly conserved among human parvovirus B19 isolates. The VIVP-1F and VIVP-1R primer pair can specifically amplify a 95 nucleotide sequence of the human parvovirus B-19 VP region. This is shown schematically in FIG. 1.

The identity of an amplification product obtained using VIVP-1F and VIVP-1R can be confirmed by hybridizing the PCR product to a PRV6 nucleic acid of the invention. The PRV6 nucleic acid of the invention is based on an oligonucleotide named VIVP-1P, which recognizes nucleotides found between the sequences amplified by the VIVP-1F and VIVP-1R primers. The VIVP-IP probe includes the sequence 5'-CACAATGCCAGTGGAAAGGAGGCAA-3' (SEQ ID NO:6), which is highly conserved among human parvovirus B19 strains.

Also within the invention are PRV7, PRV8, PRV9, and PRV10 nucleic acid sequences. These nucleic acids hybridize to regions encoding a viral polypeptide ("VP") of a porcine parvovirus genome. These sequences are based on the primers VIPPVP-1F, VIPPVP-1R, VIPPVP-1P, and VIPPVP-1F(Alt), respectively. The VIPPVP-1F primer includes the sequence 5'-GACCAAGGAGAACCAACTAA-3' (SEQ ID NO:7), while the VIPPVP-1R primer includes the sequence 5'-TTCATCAGCTGCTGAGAAGT-3' (SEQ ID NO:8). The VIPPVP-1P nucleic acid sequence includes the sequence 5'-AAAAGAACACGACGAAGCCTACGACAAATA-3' (SEQ ID NO:9), and the VIPPVP F(Alt) primer includes the sequence 5'-ACAGGACTAACTCTACCAGG-3' (SE IQ NO:10). The VIPPVP-1R primer and either the VIPPVVP-1F or VIPPVP-1F(Alt) primer can be used to amplify a region of a porcine parvovirus encoding a VP protein. The VIPPVP-1P nucleic acid hybridizes to nucleic acids located within the sequence amplified by the VIPPVP-1R primer and either the VIPPVP-1F or VIPPVP-1F(Alt) primer. Accordingly, it can be used to confirm the identity of these sequences.

In addition to detecting the presence of a parvovirus in a sample of nucleic acids, these sequences can be used to amplify a control porcine parvovirus added to a sample suspected of containing a human parvovirus sample. In one embodiment of the invention, a PRV8 (e.g., SEQ ID NO:8) and a PRV7 or PRV10 (e.g., SEQ ID NO:7 or SEQ ID NO:10 nucleic acid is added along with a porcine parvovirus to a sample suspected of containing human parvovirus B19 strain, and a primer pair including PRV1 and PRV2 (e.g., SEQ ID NO:1 and SEQ ID NO:2) or PRV4 and PRV5 (e.g., SEQ ID NO:4 or SEQ ID NO:5), or both primer pairs, and amplification products are identified. The identity of amplification products can be confirmed using the corresponding confirmatory probe for a given primer pair, e.g. PRV10 (e.g., SEQ ID NO:10) when PRV7 and PRV8 nucleic acids are used as primers, PRV3 (e.g., SEQ ID NO:3) when PRV1 and PRV2 are used as primers, or PRV6 (e.g., SEQ ID NO:6) when PRV4 and PRV5 are used as primers.

Also included in the invention are reaction systems that include a target nucleic acid, a PRV nucleic acid system, and a polymerase. The PRVX nucleic acids are preferably present in pairs to allow for PCR mediated amplification of parvovirus in a target sample. Also provided by the invention are kits containing one or more PRVX nucleic acids.

The invention also provides methods for identifying a parvovirus nucleic acid in a sample by contacting a sample containing, or suspected of containing, a parvovirus nucleic acid with a PRVX nucleic acid. In some embodiments, the methods include PCR-mediated amplification of the parvoviral nucleic acid using one or more of the PRV primer pairs described herein. The methods may be used with various biological samples including, e.g., blood and/or blood-derived compositions (e.g., clotting factors, plasma, serum).

In additional aspects, the invention includes a method of amplifying a parvovirus nucleic acid present in a target sample, as well as methods of diagnosing diseases or conditions associated with parvovirus infection.

The PRV1, PRV2, PRV3, PRV4, PRV5 and PRV6 nucleic acids hybridize to most known parvovirus B19 strains and allow for the PCR-mediated amplification of the vast majority of parvovirus B19 strains. Also included in the invention is the use of a second parvovirus and PRV nucleic acids that specifically detect the second parvovirus. The second parvovirus, which is preferably porcine parvovirus, can be added to a human nucleic acid sample and used as an internal control to facilitate the monitoring of the overall efficiency of nucleic acid extraction and the presence of potentially interfering substances within the PCR amplification reaction. The porcine parvovirus is introduced into the samples and this parvoviral DNA is co-purified and co-amplified with the B19 DNA.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 1 is a schematic illustration of the parvovirus B19 genome and the target regions which are amplified by use of the VINS and VIVP primers pairs.

DETAILED DESCRIPTION OF THE INVENTION

The invention provides nucleic acids for detecting parvovirus. The nucleic acids include PRV1, PRV2, PRV3, PRV4, PRV5, PRV6, PRV7, PRV8, PRV9, and PRV10 nucleic acids. These nucleic acids are collectively referred to herein as "PRV" nucleic acids, unless otherwise noted. They can be used, e.g., in amplification reactions, e.g., a polymerase chain reaction ("PCR"), to detect and amplify a parvovirus sample in a sample of nucleic acids.

PRVX Nucleic Acids

The PRV1, PRV2, PRV3, PRV4, PRV5, PRV6, PRV7, PRV8, PRV9, and PRV10 nucleic acids of the invention are based on oligonucleotide sequences SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10, respectively. In some embodiments, the nucleic acids PRV1, PRV2, PRV3, PRV4, PRV5, PRV6, PRV7, PRV8, PRV9, and PRV10 include SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10, respectively.

For example, included in the invention are PRV1 and PRV2 nucleic acids based on two oligonucleotides derived from a region encoding the non-structural ("NS") protein of human B19 parvovirus. The primers include VINS-3F and VINS-3R, which can be used to amplify an NS region in a polymerase chain reaction ("PCR") to amplify a noncoding sequence ("NS") region of a parvovirus genome. The VINS-3F oligonucleotide includes the nucleic acid sequence 5'-ATGGAGCTATTTAGAGGGGT-3' (SEQ ID NO:1). This sequence is highly conserved among human parvovirus strain B19 isolates. The VINS-3R oligonucleotide primer includes the sequence 5'-GTTCCCAGTCAGAAGTGTCT-3' (SEQ ID NO:2).

The PCR product generated using VINS-3F and VINS-3 can be detected using a PRV3 nucleic acid of the invention. The PRV3 nucleic acid is based on sequence of the primer 5'-TAATGTTCTGGACTGTGCTAACGAT-3' (SEQ ID NO:3), which recognizes a sequence in the region amplified by the VINS-3F and VINS-3R primers. The VINS-3F oligonucleotide is highly conserved among parvovirus strain B19 isolates and can be used to confirm the identity of the PCR product generated using VINS-3F and VINS-3R. The VINS-3F and VINS-3R primer pair can specifically amplify a 106 nucleotide sequence of a human parvovirus NS region. This region is shown in FIG. 1.

Also within the invention are PRV4 and PRV5 nucleic acids. These nucleic acids are based on oligonucleotides derived from the viral protein (VP) region of a parvovirus. The nucleic acids include VIVP-1F and VIVP-1R. A VIVP-1F nucleic acid includes the sequence 5'-CCCAGAGCACCATTATAAGGTGTT-3' (SEQ ID NO:4), which is highly conserved among parvovirus B19 isolates. A VIVP-1R nucleic acid includes the sequence 5'-TTATGGGACTAATGGTGCAAACC-3' (SEQ ID NO:5), which is also highly conserved among human parvovirus B19 isolates. The VIVP-1F and VIVP-1R primer pair can specifically amplify a 95 nucleotide sequence of the human parvovirus B-19 VP region, as is shown in FIG. 1.

The identity of an amplification product obtained using VIVP-1F and VIVP-1R can be confirmed by hybridizing the PCR product to a PRV6 nucleic acid of the invention. The PRV6 nucleic acid of the invention is based on an oligonucleotide named VIVP-1P, which recognizes nucleotides in the product amplified by the VIVP-1F and VIVP-1R primers. The VIVP-1P probe includes the sequence 5'-CACAATGCCAGTGGAAAGGAGGCAA-3' (SEQ ID NO:6), which is highly conserved among human parvovirus B19 strains.

Also within the invention are PRV7 and PRV8 nucleic acid sequences. PRV7 and PRV8 nucleic acids include those that that specifically recognize and amplify regions of a porcine parvovirus genome. In addition to detecting the presence of a parvovirus in a sample of nucleic acids, these sequences can be used to amplify a control porcine parvovirus added to a sample suspected of containing a human parvovirus sample. PRV7 and PRV8 nucleic acid sequences are based on porcine primers and are designated VIPPVP-1F and VIPPVP-1R, respectively. These primers are specific for a region encoding the structural viral protein (VP) of a porcine parvovirus nucleic acid. The VIPPVP-1F nucleic acid sequence includes 5'-GACCAAGGAGAACCAACTAA-3' (SEQ ID NO:7). The VIPPVP-1R primer includes the sequence 5'-TTCATCAGCTGCTGAGAAGT-3' (SEQ ID NO:8). While these primers possess a very high degree of homology (i.e., 70–100%) to other animal parvoviruses, they lack sequence homology to both human genomic sequences or other human viral sequences. The amplified product of VIPPVP-1F and VIPPVP-1R is 117 nucleotides.

An alternative nucleic acid for amplifying porcine parvoviral nucleic acids is PRV10, which is based on the sequence VIPPVP-1F(Alt), which includes the sequence 5'-ACAGGACTAACTCTACCAGG-3' (SE IQ NO:10). The sequence is located at 2358–2377 of the VP region. It produces a 168 bp PCR product when used in combination with the VIPPVP-1R primer.

The identity of an amplification product obtained using either VIPPVP-1F or VIPPVP-1F(Alt) and VIPPVP-1R can be confirmed by hybridizing the product to a PRV9 nucleic acid according to the invention. A PRV9 nucleic acid is based on an oligonucleotide probe named VIPPVP-1P. The VIPPVP-1P nucleic acid sequence includes the sequence 5'-AAAAGAACACGACGAAGCCTACGACAAATA-3' (SEQ ID NO:9). The VIPPVP-1P nucleic acid is highly homologous to regions of other porcine B19 isolates.

In one aspect, the invention provides a PRVX nucleic acid molecule. As nucleic acids do not require complete homology to hybridize, it will be apparent to those skilled in the art that the primer sequences specifically disclosed herein may be modified so as to be substantially homologous to the primer sequences disclosed herein without loss of utility as parvovirus specific detection and/or amplification primers. It is well-known in the art that hybridization of homologous and partially homologous nucleic acid sequences may be accomplished by adjusting the hybridization conditions to increase or decrease the stringency (i.e., adjusting the hybridization temperature or salt content of the buffer). Accordingly, a PRVX nucleic acid molecule according to the invention can be provided as an oligonucleotide, e.g., and can be less than about 100, e.g., 50, 31, 36, 25, 24, 23 or 22, and which includes at least 15 nucleotides of the corresponding sequence SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments, and homologs thereof. The nucleic acid molecule may be single-stranded or double-stranded, but preferably is comprised double-stranded DNA. In some embodiments, the PRV nucleic acid is specific for a NS sequence of a parvovirus. In other embodiments, the PRV nucleic acid is specific for a VP-encoding region of a parvovirus. Preferably, the PRV nucleic acid is homologous to a NS or VP-encoding region that is highly conserved among multiple PRV isolates. When a PRV nucleic acid is used as a primer in an extension reaction, it is provided with an extendible terminus, e.g., a 3' OH terminus, that can be extended by a polymerase.

In some embodiments, a PRVX nucleic acid molecule according to the invention forms a stable duplex with a target nucleic acid sequence at a temperature higher than 37° C., e.g., at greater than, 50° C., 55° C., 60° C., 65° C., 70° C., or more degrees.

In some embodiments, the PRVX nucleic acid molecule hybridizes to a region of a parvovirus genome but does not hybridize in significant amounts to an endogenous mammalian nucleic acid sequence, e.g., an endogenous non-viral human nucleic acid sequence.

A PRVX nucleic acid can be provided as a member of a pair of PRVX nucleic acids that, together, amplify a region of a parvovirus, e.g., in a PCR reaction. In some embodiments, the pair of PRV nucleic acids amplify a region encoding an NS polypeptide of a parvovirus, e.g., a NS encoding region of a human parvovirus such as human strain B19 parvovirus. Examples of a NS primer pair include PRV1 and PRV2, e.g., an oligonucleotide including SEQ ID NO:1 and SEQ ID NO:2.

In other embodiments, the pair of PRV nucleic acids hybridizes to a viral protein encoding region of a parvovirus, e.g., a VP encoding region of a human parvovirus such as human strain 19 parvovirus. Examples of a VP primer pair include, e.g., PRV4 and PRV5, e.g., SEQ ID NO:3 and SEQ ID NO:4. Additional examples of pairs of PRV-nucleic acids that are specific for a VP encoding region is PRV7 and PRV8; and PRV10 an PRV8, PRV 10, and PRV8, e.g., SEQ ID NO:7 and SEQ ID NO:8; and SEQ ID NO; 10 and SEQ ID NO:8. PRV7, PRV8, and PRV10 detect a nucleic acid encoding a porcine parvovirus VP.

The term "probes", as utilized herein, includes nucleic acid sequences of variable length, preferably between at least about 10 nucleotides (nt) to about 1000 nt. The probes can be provided as oligonucleotides. As used herein, the term "oligonucleotide" refers to a series of linked nucleotide residues, in which oligonucleotide has a sufficient number of nucleotide bases to be used in a subsequent amplification reaction, e.g., a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt–1000 nt, e.g., 12 nt, 13 nt, 14 nt, 15 nt, 17 nt, 18 nt, 19 nt, 20 nt, 21 nt, 22 nt, 23 nt, 24 nt, 25 nt, 31 nt, 50 nt, or 100 nt, 500 nt, or fewer nucleotides in length. Preferably, the oligonucleotides are about 18–22 nt in length, depending upon the specific use. Probes are used in the detection of identical, similar, or complementary nucleic acid sequences. Probes may be single- or double-stranded and designed to have specificity in PCR, membrane-based hybridization technologies, or ELISA-like technologies.

A PRVX nucleic acid according to the invention can be provided as an isolated nucleic acid molecule. The term "isolated" nucleic acid molecule, as utilized herein, is one that is separated from other nucleic acid molecules which are present in the natural source of the nucleic acid. Preferably, an "isolated" nucleic acid is free of sequences which naturally flank the nucleic acid (i.e., sequences located at the 5'- and 3'-terrnini of the nucleic acid) in the genomic DNA of the organism from which the nucleic acid is derived.

A PRVX nucleic acid molecule of the invention can be chemically synthesized using well-known techniques for constructing nucleic acids, and the sequence information provided herein. Alternatively, a nucleic acid molecule of the invention can be isolated using standard molecular biology techniques (e.g., as described in Sambrook, et al., (eds.), MOLECULAR CLONING: A LABORATORY MANUAL $2^{nd}$ Ed., Cold Spring Harbor Laboratory Press, Cold Spring Harbor, N.Y., 1989; and Ausubel, et al., (eds.),

*Current Protocols in Molecular Biology*, John Wiley & Sons, New York, N.Y., 1993.)

For example, a PRVX nucleic acid can be amplified using cDNA, mRNA or alternatively, genomic DNA, as a template and appropriate oligonucleotide primers according to standard PCR amplification techniques. The nucleic acid so amplified can be cloned into an appropriate vector and further characterized by DNA sequence analysis. Furthermore, oligonucleotides can be prepared by standard synthetic techniques, e.g., using an automated DNA synthesizer.

The PRVX nucleic acid molecules in the invention can include modified nucleotides. Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

One or more of the PRVX nucleic acid molecules according to the invention can be provided with a label group attached thereto. For example, the label group can be a radioisotope, a fluorescent compound, an enzyme, or an enzyme co-factor. Such probes can be used as a part of a diagnostic test kit for identifying cells or tissue which contain parvovirus nucleic acid sequences (either parvovirus DNA or RNA, or both), such as by measuring a level of a parvovirus nucleic acid in a sample of cells from a subject.

A label is a substance that can be covalently attached to or firmly associated with a nucleic acid probe that will result in the ability to detect the probe. For example, a level may be a radioisotope, an enzyme substrate or inhibitor, an enzyme, a radiopaque substance (including colloidal metals), a fluorescers, a chemiluminescent molecule, liposomes containing any of the above labels, or a specific binding pair member. A suitable label will not lose the quality responsible for detectability during amplification.

Those skilled in the diagnostic art will be familiar with suitable detectable labels for use in in vitro detection assays. For example, suitable radioisotopes for in vitro use include $^3H$, $^{121}I$, $^{32}P$, $^{34}C$, and $^{35}S$. Radio-labeled amplified fragments may be detected directly by gamma counter or by densitometry of autoradiographs, by Southern blotting of the amplified fragments combined with densitometry.

Examples of suitable chemiluminescent molecules are acridines or luminol. Target sequences hybridized with probes derivatized with acridium ester are protected from hydrolysis by intercalation. Examples of suitable fluorescers are fluorescein, phycobiliprotein, rare earth chelates, dansyl or rhodamine.

The term "labeled" is intended to encompass direct labeling of the probe by coupling (i.e., physically linking) a detectable substance to a PRV nucleic acid, as well as indirect labeling of a PRV nucleic acid by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin.

Detection Systems and Kits for Identifying Parvovirus Nucleic Acids

Also provided in the invention is a nucleic acid detection system for detecting a target nucleic acid. The system includes a target nucleic acid, one or more PRVX nucleic acids that can hybridize specifically to a parvovirus nucleic acid, and a polymerase. The system can additionally include, e.g., a control parvovirus. A preferred control parvovirus is porcine parvovirus. The system may further include reaction buffers, labels, and detection means for identifying labeled nucleic acids, e.g., labeled amplification products indicative of the presence of a parvovirus nucleic acid in the sample.

In some embodiments, two or more PRVX nucleic acids are provided in the detection system. For example, the PRV nucleic acids can be provided as a pair of PRV1 and PRV2 nucleic acids, e.g., a pair of oligonucleotides in which a PRV1 is a primer less than 31 nucleotides in length and which includes at least 15 nucleotides of SEQ ID NO:1, and a PRV2 nucleic acid is provided as a second primer less than 31 nucleotides in length and which includes at least 15 nucleotides of SEQ ID NO:2. If desired, a PRV3 nucleic acid, e.g., a nucleic acid that includes SEQ ID NO:3, can also be included in the sample.

In other embodiments, the PRV nucleic acids are provided as a pair of PRV4 and PRV5 nucleic acids. For example, the PRV4 nucleic acid can include a primer less than 31 nucleotides in length and which includes at least 15 nucleotides of SEQ ID NO:4. The PRV5 nucleic acid can be provided as a primer less than 31 nucleotides in length and including at least 15 nucleotides of SEQ ID NO:5. If desired, a PRV6 nucleic acid, e.g., a nucleic acid that includes SEQ ID NO:6, can be included in the sample.

In a further embodiment, the PRV nucleic acids in the detection system can be provided as a pair of either PRV7 or PRV10, and PRV8 nucleic acids. For example, the PRV7 nucleic acid can be provided as a primer less then 31 nucleotides in length and comprising at least 15 nucleotides of SEQ ID NO:7, the PRV10 nucleic acid can be provided as a primer less then 31 nucleotides in length and comprising at least 15 nucleotides of SEQ ID NO: 10, and the PRV8 nucleic acid can be provided as a primer less than 31 nucleotides in length and comprising at least 15 nucleotides of SEQ ID NO:8. If desired, a PRV9 nucleic acid, e.g., a nucleic acid that includes SEQ ID NO:9, can be included in the sample.

In still further embodiments, the reaction system includes multiple pairs of PRVX nucleic acids. For example, the reaction system can include two or more pairs of a PRV1 and PRV2 nucleic acid (and optionally a PRV3 nucleic acid), a PRV4 and PRV5 nucleic acid (and optionally a PRV6 nucleic acid), and a PRV8 nucleic acid and either PRV7 or PRV10 nucleic acid (and optionally a PRV9 nucleic acid).

The invention also encompasses kits for detecting the presence of a parvovirus nucleic acid in a biological sample. For example, the kit can include one or more PRVX nucleic acids. The kit may alternatively, or in addition, include a control parvovirus (e.g., a porcine parvovirus) or control parvovirus nucleic acid, a labeled compound or agent capable of detecting parvovirus DNA or mRNA in a biological sample, a means for determining the amount of a parvovirus nucleic acid in the sample; and a means for comparing the amount of parvovirus in the sample with a standard. The compound or agent can be packaged in a suitable container. The kit can further comprise instructions for using the kit to detect a parvovirus nucleic acid.

Method of Detecting a Parvovirus Nucleic Acid

The invention also provides a method of detecting a nucleic acid molecule, e.g., a parvovirus nucleic acid molecule, in a sample of nucleic acid molecules. The method includes providing a sample that includes a target nucleic acid molecule, contacting the sample with a PRV nucleic acid under conditions that allow for formation of a stable duplex between the annealed PRV nucleic acid and the target nucleic acid molecule. The annealed PRV nucleic acid can be detected directly, if desired. Alternatively, the annealed target nucleic acid molecule complex can be extended with a polymerase to form a first extended primer sequence. The extended primer sequence is identified, thereby identifying the target nucleic acid molecule in the sample of nucleic acid molecules.

In some embodiments, the first extended primer sequence is contacted with a second PRV nucleic acid to form a second annealed primer-target nucleic acid molecule complex. The second annealed target nucleic acid molecule complex is then extended with a polymerase to form a second extended primer sequence. The second extended primer sequence can be detected, if desired, or can be hybridized to the first PRV nucleic acid and used in additional cycles of amplification.

In some embodiments, a reference parvovirus is added to the sample, and one or more PRV nucleic acids capable of specifically detecting the reference parvovirus are added. A preferred reference parvovirus is porcine parvovirus, and preferred PRVX nucleic acids for detecting the parvovirus is PRV7, PRV8, PRV9, and PPRV10.

Extension with a polymerase can be used in conjunction with in any method of nucleic acid amplification known in the art. Any polymerase known in the art can be used. One of ordinary skill in the art will a recognize, for example, that an RNA-directed polymerase can be used when the PRVX nucleic acid is provided as an RNA molecule, and a DNA-directed DNA polymerase can be used when the PRVX nucleic acid is provided as a DNA molecule. Polymerase-based extension methods include, e.g., Polymerase Chain Reaction (PCR; described in U.S. Pat. Nos. 4,683,195, 4,683,202, 4,800,159, 4,965,188). PCR is an in vitro method for the enzymatic synthesis of specific DNA or RNA sequences using oligonucleotide primers that hybridize to specific nucleic acid sequences and flank the region of interest in target nucleic acid. A repetitive series of cycles of template denaturation, primer annealing and enzymatic extension of the annealed primers results in an exponential accumulation of a specific nucleic acid fragment defined at its termini by the 5' ends of the primers. The resulting products (PCR products) synthesized in one cycle act as templates for the next; consequently, the number of target nucleic acid copies approximately doubles in every cycle.

PCR techniques are described in, e.g., U.S. Pat. Nos. 4,683,195 and 4,683,202 to Mullis et al, the disclosures of which are incorporated herein as examples of the conventional techniques for performance of the PCR. The methods may also use assays that have been developed which utilize modifications of that technique. These modifications are well-known in the art A PCR technique which provides an internal amplification standard using a competitor template which differs from the target nucleic acid in sequence and size is described in Gilliland et al., Proc.Natl.Acad.Sci.USA 87:2725–29 (1990). Another technique for performing "competitive" PCR which uses templates which differ in sequence but not in size is described in Kohsaka et al., Nuc. Acids. Res. 21:3469–72 (1993). This technique is a particularly preferred technique for its use of enzyme-linked immunoabsorbent assay (ELISA) technology to analyze the amplified nucleic acid(s). A noncompetitive PCR technique which utilizes site-specific oligonucleotides to detect mutations or polymorphisims in genes which may also be applied to the method of the invention is described in Saike et al., Proc-.Natl.Acad.Sci.USA (1989) 86:6230–34.

For further background, those skilled in the art may wish to refer to Innis, et al., "Optimization of PCR's", PCR Protocols: A Guide to Methods and Applications (Acad.Press, 1990). This publication summarizes techniques to influence the specificity, fidelity and yield of the desired PCR products.

Other amplification techniques include, e.g., Strand Displacement Amplification (SDA; described by G. Walker et al., Proc. Nat. Acad. Sci. USA 89, 392 (1992); G. Walker et al., Nucl. Acids Res. 20, 1691 (1992); U.S. Pat. No. 5,270, 184, the disclosure of which is hereby incorporated in its entirety by reference), thermophilic Strand Displacement Amplification (tSDA; EP 0 684 315 to Frasier et al.), Self-Sustained Sequence Replication (3SR; J. C. Guatelli et al., Proc Natl. Acad. Sci. USA 87, 1874–78 (1990)), Nucleic Acid Sequence-Based Amplification (NASBA; U.S. Pat. No. 5,130,238 to Cangene), the Q.crclbar. replicase system (P. Lizardi et al., BioTechnology 6, 1197 (1988)), or transcription based amplification (D. Y. Kwoh et al., Proc. Natl. Acad. Sci. USA 86, 1173–77 (1989)).

For use in the methods of the invention, a biological sample is obtained which is suspected of containing parvovirus nucleic acid, e.g., a human parvovirus nucleic acid. For example, the sample may comprise body fluid or cells, e.g., from a cell line, tissue or tumor. Such samples are obtained using methods known in the clinical art, e.g., tumor cells may be acquired by biopsy or surgical resection. Preferably, the cells are essentially free from "contaminants"; e.g., cells, proteins and similar components which are likely to falsify the result of the method of the invention.

Alternatively, samples can be obtained from purified, or partially purified biological fluids, e.g., blood products, or blood-derived products.

The nucleic acid to be amplified in the sample will include genomic or wild-type DNA which would normally be expected to contain parvovirus. This DNA to be amplified is obtainable from a eukaryote, preferably a mammal, e.g., a human. The sample containing the DNA of interest can be any biological sample, e.g., cells, tissues, and bodily fluids. Cells can include, e.g., erythroid precursor cells. Bodily fluids can include, e.g., blood, blood-derived products, blood-associated components such as plasma, serum or other blood-derived products. Biological fluids can also include, e.g., respiratory secretions, feces, urine, synvovial fluid, cerebrospinal fluid, lymphatic fluid and semen.

Nucleic acids can be isolated according to methods known in the art, e.g., the method described by Maniatis, et al. (Molecular Cloning, A Laboratory Manual, Cold Spring Habor Laboratory, 1982). However, those skilled in the art will recognize that other suitable means of obtaining nucleic acids can be used.

Once the sample is obtained, the sample containing (or suspected of containing) parvovirus nucleic acid it is subjected to conditions favoring the selective amplification of the target nucleic acid. Preferably, the target nucleic acid will be a polynucleotide portion of a parvovirus sequence (i.e., the "target polynucleotide"). Preferably, the target polynucleotide is amplified by PCR.

Once the amplification step is complete, the PCR products are assayed to determine whether a parvovirus nucleic acid is present in the sample. For example, the double-stranded PCR products can be bound to a solid-phase so their strands may be separated by denaturation. This technique allows sequence-specific probes to hybridize to the bound antisense strand of the PCR product to detect the gene. Alternatively, the PCR products can be removed from the reaction environment and separated from the amplification mixture prior to the addition of probes for hybridization to the double-stranded PCR products. In this latter approach, the PCR products are separated from the amplification mixture according to methods known in the art with regard to the particular method chosen for detection; e.g., by gel exclusion, electrophoresis, or affinity chromatography.

Detection of the amplified product may also be achieved by using hybridization probes which are stably associated with a detectable label. Examples of suitable enzyme substrates or inhibitors are compounds which will specifically-bind to horseradish peroxidase, glucose oxidase, glucose-6-phosphate dehydrogenase, beta-galactosidase, pyruvate kinase, or alkaline phosphatase acetylcholinesterase. Examples of radiopaque substance are colloidal gold or magnetic particles. The failure to detect sequences homologous to a PRVX nucleic acid indicates that no parvovirus is present in the sample.

In some embodiments, a control parvovirus nucleic acid is added to the sample, along with PRVX probes that detect the control nucleic acid. Preferably the control nucleic acid does not hybridize to PRV nucleic acids used to detect the parvovirus nucleic acid in the sample of target nucleic acids. For example, when the target nucleic acid is a human parvovirus, and PRV1 and PRV2 nucleic acids or PRV4 and PRV5 nucleic acids are used in the sample, a preferable control parvovirus nucleic acid is porcine parvovirus nucleic acid. The control porcine parvovirus is preferably detected using PRV7 and PRV8 probes.

Preferably, the porcine parvovirus nucleic acid is provided as a virus. The addition of a control virus allows for the recovery of nucleic acid in the test sample to be monitored. For example, when porcine parvovirus is added to the sample before sample centrifugation and nucleic acid extraction, the amount of sample lost to sample manipulation, e.g., during sample centrifugation, nucleic acid extraction, can be assessed. The presence of potentially inhibitory substances interfering with nucleic acid hybridization and amplification can also be determined. Introduction of a control nucleic acid thus minimizes the potential for false negative results.

The invention also provides a method of amplifying a parvovirus nucleic acid in a target nucleic acid molecule. The method includes providing a sample that includes a target nucleic acid molecule, contacting the sample with one or more PRVX nucleic acids, e.g., at least one member of a primer pair that includes PRV1 and PRV2 nucleic acids, a PRV4 and PRV5 nucleic acid, and/or a PRV7 and PRV8 nucleic acids. The PRVX nucleic acid is contacted under conditions that allow for annealing of the PRVX nucleic acid to a parvovirus target nucleic acid in the sample under conditions that allow for formation of a annealed primer-target nucleic acid molecule complex. The complex is extended with a polymerase to form a first extended primer sequence, thereby amplifying said target nucleic acid molecule. If desired, the first extended primer sequence is contacted with the second member of the primer pair to form a second annealed primer-target nucleic acid molecule complex, and the second annealed target nucleic acid molecule complex is extended with a polymerase to form a second extended primer sequence.

Also within the invention are methods of diagnosing a disease or condition, or assessing a susceptibility to a disease or condition, based on the presence of a parvovirus nucleic acid in the sample. The method includes providing a nucleic acid from a subject, e.g., a human subject, suspected of having or being at risk for, the parvovirus-associated disease. The sample is contacted with one or more PRVX nucleic acids, e.g., at least one member of a primer pair that includes PRV1 and PRV2 nucleic acids, a PRV4 and PRV5 nucleic acid, and/or a PRV7 and PRV8 nucleic acids. The PRVX nucleic acid is contacted under conditions that allow for annealing of the PRVX nucleic acid to a parvovirus target nucleic acid in the sample under conditions that allow for formation of an annealed primer-target nucleic acid molecule complex. The complex can be detected directly, if desired. Alternatively, the complex annealed parvovirus target is amplified, and the amplified product is detected. Amplification can occur by extending the complex with a polymerase to form a first extended primer sequence. If desired, the first extended primer sequence is contacted with the second member of the primer pair to form a second annealed primer-target nucleic acid molecule complex, and the second annealed target nucleic acid molecule complex is extended with a polymerase to form a second extended primer sequence. The presence of the complex, or of the amplified parvovirus nucleic acid, indicates the presence of, or susceptibility to, of the disease, in the subject.

The parvovirus associated diseases or conditions can include, e.g., aplastic crises, including transient aplastic crises occurring as a result of cessation of erythropoiesis. Transient aplastic crisis (TAC) is the abrupt cessation of erythropoiesis characterized by reticulocytopenia, absent erythroid precursors in the bone marrow and precipitous worsening of anemia. TAC, due to B19 infection, has been described in a wide-range of patients with underlying hemolytic disorders, including, e.g., hereditary spherocytosis; thalassemia; red cell enzymopathies (e.g., pyruvate kinase deficiency), and autoimmune hemolymic anemia. Other diseases include, e.g., erythema infectiosum (which is also referred to as fifth disease, slapped disease, academy rash, Sticker's disease), polyarthorpathy syndrome, hydrops, myocarditis, and neurological disease.

The invention will be further illustrated in the following examples, which do not limit the scope of the appended claims.

EXAMPLE 1

PCR Amplification and Detection of Parvovirus Using PRVX Nucleic Acids

PCR-mediated amplification is performed using a multiplexed or single primer pair reaction tube. The multiplexed reaction includes the addition of the NS primers VINS-3F and VINS-3R, the VP primers VIVP-1F and VIVP-1R, and the porcine parvovirus primers VIPPVP-1F and VIPPVP-1R to a single reaction tube. The amplification reaction results in the formation of three PCR products: one for the NS region; one for the VP region; and one for the VP region of the PPV internal control. The single primer pair reaction amplification is performed in three separate reaction tubes: one containing the NS primers; one containing the VP primers; and one containing the PPVVP primer.

Three primer pairs are used within individual tubes which contain the following reaction mixtures: 10–20 μM of each primer, 1×Reaction Buffer (10 mM Tris-HCl, pH 8.3; 50 mM KCl), 2.0–4.0 mM MgCl$_2$, 200–300 μM each of dATP, dGTP, dCTP and dTTP (the dTTP is usually substituted with 200–600 μM of dUTP when AmpErase® is used), 0.2 to 1.0 units of AmpErase®, and 1–2 units of Taq polymerase. Amplification is achieved through 40–43 PCR cycles consisting of: denaturing at 95° C. for 10–30 seconds, annealing at 55–62° C. for 15–45 seconds, and extension at 72° C. for 15–45 seconds, followed by 10 minutes at 72° C.

The three primer pairs are used together in a single reaction tube (i.e., all primers contained within one tube).

The resulting PCR products are detected using two different methods.

Method 1: PCR products are separated by agarose and/or polyacrylamide gel electrophoresis, stained with SYBR green dye (Molecular Probes, Eugene, OR), ethidium bromide, and visualized by exposure to a suitable light source, e.g. 254 nm UV light source. The product is identified as B19-specific or PPV-specific by liquid or Southern blot hybridization with the specific B19 or PPV probes previously discussed in Sections 1–3.

Method 2: The second method of detection is based upon fluorophore-labeled probes that hybridize to the specific PCR product (i.e., B19 or PPV) and emits light of a known-wave length upon exposure to a UV light. These detection methods include the TaqMan® and Molecular Beacons® detection methods developed by Roche Molecular Systems, Inc. New Jersey and Dr. Fred Kramer Public Health Research Institute, New York, respectively. The emitted light, which is a function of the overall quantity of the PCR products, can be quantitated by use of a very sensitive diode detector. The later system allows amplification and detection of multiple targets in the same PCR by labeling each probe with a different fluorophore.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of detecting a parvovirus nucleic acid molecule in a sample of nucleic acid molecules, the method comprising:
   providing a sample comprising a target nucleic acid molecule;
   contacting said sample with at least one member of a plurality of primer pairs under conditions that allow annealing of said at least one member to a homologous target nucleic acid molecule in said sample, thereby forming a plurality of first annealed primer-target nucleic acid molecule complexes, wherein said plurality of primer pairs includes
      a first pair comprising a first primer less than 31 nucleotides in length and comprising at least 15 nucleotides of SEQ ID NO:1 and a second primer less than 31 nucleotides in length and comprising at least 15 nucleotides of SEQ ID NO:2;
      a second pair comprising a third primer less than 31 nucleotides in length and comprising at least 15 nucleotides of SEQ ID NO:4, and a fourth primer less than 31 nucleotides in length and comprising at least 15 nucleotides of SEQ ID NO:5;
   extending said plurality of first annealed target nucleic acid molecule complexes with a polymerase to form a plurality of said first extended primer sequences; and
   identifying said plurality of extended primer sequences, thereby identifying a nucleic acid molecule in said sample of nucleic acid molecules.

2. The method of claim 1, further comprising
   contacting the first extended primer sequence with the second member of said plurality of primer pairs to form a plurality of second annealed primer-target nucleic acid molecule complexes; and
   extending said plurality of second annealed primer-target nucleic acid molecule complexes to form a plurality of second extended primer sequences.

3. The method of claim 1, wherein at least one of said first primer, second primer, or fourth primer comprises the nucleotide sequence of SEQ ID NO:1, SEQ ID NO:2, SEQ ID NO:4, or SEQ ID NO:5.

4. The method of claim 1, wherein at least two of said first primer, second primer, third primer, or fourth primer comprise the nucleotide sequence of SEQ ID NO:1, SEQ ID NO:2, SEQ ID NO:4, or SEQ ID NO:5.

5. The method of claim 1, wherein at least three of said first primer, second primer, third primer, or fourth primer comprise the nucleotide sequence of SEQ ID NO:1, SEQ ID NO:2, SEQ ID NO:4, or SEQ ID NO:5.

6. The method of claim 1, wherein said first primer, second primer, third primer, and said fourth primer comprise the nucleotide sequence of SEQ ID NO:1, SEQ ID NO:2, SEQ ID NO:4, or SEQ ID NO:5.

7. The method of claim 1, wherein said sample includes a reference parvovirus nucleic acid.

8. The method of claim 7, wherein said reference parvovirus is a porcine parvovirus.

9. The method of claim 1, wherein said method further comprises contacting said sample with at least one member of a third primer pair under conditions that allow annealing of said at least one member to a homologous target nucleic acid molecule in said sample, thereby forming a plurality of first annealed primer-target nucleic acid molecule complexes, wherein said third primer pair includes a fifth primer less than 31 nucleotides in length and comprising at least 15 nucleotides of SEQ ID NO:7 and a sixth primer less than 31 nucleotides in length and comprising at least 15 nucleotides of SEQ ID NO:8;
   extending said at least one member of said third primer pair with a polymerase to form a third extended primer sequence; and
   detecting said third extended primer sequence.

10. The method of claim 9, wherein said fifth primer comprises SEQ ID NO:7 or SEQ ID NO:10.

11. The method of claim 9, wherein said sixth primer comprises SEQ ID NO:8.

12. The method of claim 10, wherein said sixth primer comprises SEQ ID NO:8.

13. A method for diagnosing the presence or susceptibility associated with a disease or condition associated with parvovirus infection in a subject, the method comprising
   providing a sample comprising a target nucleic acid molecule;
   contacting said sample with at least one member of a plurality of primer pairs under conditions that allow annealing of said at least one member to a homologous target nucleic acid molecule in said sample, thereby forming a plurality of first annealed primer-target nucleic acid molecule complexes, wherein said plurality of primer pairs includes
      a first pair comprising a first primer less than 31 nucleotides in length and comprising at least 15 nucleotides of SEQ ID NO:1 and a second primer less than 31 nucleotides in length and comprising at least 15 nucleotides of SEQ ID NO:2;
      a second pair comprising a third primer less than 31 nucleotides in length and comprising at least 15 nucleotides of SEQ ID NO:4, and a fourth primer less than 31 nucleotides in length and comprising at least 15 nucleotides of SEQ ID NO:5;
   extending said plurality of first annealed target nucleic acid molecule complexes with a polymerase to form a plurality of said first extended primer sequences; and
   identifying said plurality of extended primer sequences, wherein the identification of said plurality indicates that said subject has or susceptible to a disease or condition associated with parvoviris infection.

14. The method of claim 13, further comprising
   contacting the first extended primer sequence with the second member of said plurality of primer pairs to form a plurality of second annealed primer-target nucleic acid molecule complexes; and
   extending said plurality of second annealed primer-target nucleic acid molecule complexes to form a plurality of second extended primer sequences.

15. The method of claim 13, wherein at least one of said first primer, second primer, third primer, or fourth primer comprises the nucleotide sequence of SEQ ID NO:1, SEQ ID NO:2, SEQ ID NO:4, or SEQ ID NO:5.

16. The method of claim 13, wherein at least two of said first primer, second primer, third primer, or fourth primer comprise the nucleotide sequence of SEQ ID NO:1, SEQ ID NO:2, SEQ ID NO:4, or SEQ ID NO:5.

17. The method of claim 13, wherein at least three of said first primer, second primer, third primer, or fourth primer comprise the nucleotide sequence of SEQ ID NO:1, SEQ ID NO:2, SEQ ID NO:4, or SEQ ID NO:5.

18. The method of claim 13, wherein said first primer, second primer, third primer, and said fourth primer comprise the nucleotide sequence of SEQ ID NO:1, SEQ ID NO:2, SEQ ID NO:4, or SEQ ID NO:5.

19. The method of claim 13, wherein said sample includes a reference parvovirus nucleic acid.

20. The method of claim 13, wherein said reference parvovirus is a porcine parvovirus.

21. The method of claim 20, wherein said method further comprises contacting said sample with at least one member of a third primer pair under conditions that allow annealing of said at least one member to a homologous target nucleic acid molecule in said sample, thereby forming a plurality of first annealed primer-target nucleic acid molecule complexes, wherein said third primer pair includes a fifth primer less than 31 nucleotides in length and comprising at least a 15 nucleotides of SEQ ID NO:7 and a sixth primer less than 31 nucleotides in length and comprising at least 15 nucleotides of SEQ ID NO:8;

extending said at least one member of said third primer pair with a polymerase to form a third extended primer sequence; and detecting said third extended primer sequence.

22. The method of claim 21, wherein said fifth primer comprises SEQ ID NO:7 or SEQ ID NO:10.

23. The method of claim 21, wherein said sixth primer comprises SEQ ID NO:8.

24. The method of claim 22, wherein said sixth primer comprises SEQ ID NO:8.

* * * * *